United States Patent
Strahl

(10) Patent No.: US 9,044,155 B2
(45) Date of Patent: Jun. 2, 2015

(54) STIMULUS ARTIFACT REMOVAL FOR NEURONAL RECORDINGS

(75) Inventor: Stefan Strahl, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1009 days.

(21) Appl. No.: 12/559,715

(22) Filed: Sep. 15, 2009

(65) Prior Publication Data

US 2010/0069996 A1 Mar. 18, 2010

Related U.S. Application Data

(60) Provisional application No. 61/097,611, filed on Sep. 17, 2008.

(51) Int. Cl.
- *A61N 1/00* (2006.01)
- *A61B 5/04* (2006.01)
- *G06K 9/00* (2006.01)
- *G06K 9/62* (2006.01)
- *A61N 1/05* (2006.01)

(52) U.S. Cl.
CPC ............ *A61B 5/04001* (2013.01); *A61N 1/0541* (2013.01); *G06K 9/00523* (2013.01); *G06K 9/624* (2013.01)

(58) Field of Classification Search
CPC ............. A61B 5/7217; A61B 5/04001; A61N 1/0541; A61N 1/36032; A61N 1/3065; A61N 1/36117; G06K 9/00523
USPC .......................................... 607/13, 28, 55–57
See application file for complete search history.

(56) References Cited

U.S. PATENT DOCUMENTS

| | | | | |
|---|---|---|---|---|
| 6,157,861 | A * | 12/2000 | Faltys et al. ..................... | 607/57 |
| 6,847,737 | B1 | 1/2005 | Kouri et al. ................... | 382/260 |
| 2006/0069322 | A1* | 3/2006 | Zhang et al. .................. | 600/512 |
| 2006/0287609 | A1* | 12/2006 | Litvak et al. .................. | 600/554 |
| 2007/0118047 | A1* | 5/2007 | Tracey et al. .................. | 600/554 |
| 2007/0255504 | A1* | 11/2007 | Noma et al. .................... | 702/19 |
| 2008/0051647 | A1* | 2/2008 | Wu et al. ........................ | 600/382 |
| 2008/0183090 | A1* | 7/2008 | Farringdon et al. ........... | 600/509 |

OTHER PUBLICATIONS

Wu, Y. et al, Filtering of noise in electrocardiographic signals using an unbiased and normalized adaptive artifact cancellation system, Oct. 2007, Proceedings of NFSI & ICFBI, pp. 173-176.*
Hashimoto et al, A template subtraction method for stimulus artifact removal in high-frequency deep brain stimulation. J. Neurosci. Methods, 2002; 113: 181-6.*
European Patent Office, International Search Report and Written Opinion, PCT/IB2009/006997; Feb. 26, 2010.

* cited by examiner

*Primary Examiner* — Niketa Patel
*Assistant Examiner* — William Levicky
(74) *Attorney, Agent, or Firm* — Sunstein Kann Murphy & Timbers LLP

(57) ABSTRACT

A method is described for processing an electrical stimulation response measurement waveform signal measured in response to delivery of a selected electrical stimulation signal to neural tissue. The electrical stimulation response measurement waveform signal contains a stimulus artifact and one or more neuronal action potentials. The electrical stimulation signal is selected based on satisfying a cost function comparison between at least one stimulus artifact component and a plurality of known neuronal action potential waveforms. The electrical stimulation response waveform signal is then processed using a source separation algorithm to remove the stimulus artifact component.

8 Claims, 2 Drawing Sheets

STIMULUS ARTIFACT REMOVAL FOR NEURONAL RECORDINGS

This application claims priority from U.S. Provisional Patent Application 61/097,611, filed Sep. 17, 2008, which is incorporated herein by reference.

FIELD OF THE INVENTION

The present invention relates to medical implants, and more specifically to diagnostic measurement in cochlear implant systems.

BACKGROUND ART

Recordings of neuronal action potentials (NAPs) evoked by close-by applied electrical stimulation provide a signal mixture containing two major components: (1) the desired NAPs, and (2) the applied electrical stimulus. The removal of the unintentional recorded stimulus waveform (also called the stimulus artifact) from this mixture has proven to be a difficult task.

Various techniques have been used to eliminate or reduce the stimulus artifact from recordings of evoked compound action potentials (ECAP) in neuroprosthetic devices such as cochlear implants. In the alternating stimulation approach, two recordings are performed using anodic-cathodic and cathodic-anodic biphasic stimulation pulses. See Eisen M D, Franck K H, *Electrically Evoked Compound Action Potential Amplitude Growth Functions and HiResolution Programming Levels in Pediatric CII Implant Subjects*, Ear & Hearing 2004, 25(6):528-538, incorporated herein by reference. The NAPs are assumed to be independent of the polarity of the first phase, so the stimulus artifact can be averaged out. But alternating stimulation creates an undesired increase in measurement time. Moreover, the assumption of phase-invariance of an NAP does not hold completely.

In the masker probe method, a second probe pulse is sent within the neuron's refractory time which allows a template for the stimulus artifact to be measured. See Brown C, Abbas P, Gantz B, *Electrically Evoked Whole-Nerve Action Potentials: Data From Human Cochlear Implant Users*, Journal of the Acoustical Society of America 1990, 88(3):1385-1391, and Miller C A, Abbas P J, Brown C J, *An Improved Method Of Reducing Stimulus Artifact In The Electrically Evoked Whole-Nerve Potential*, Ear & Hearing 2000, 21(4):280-290; which are incorporated herein by reference. As with alternating stimulation, the masker probe approach requires an undesirable increase in measurement time. In addition, some of the nerves typically are not in a refractory state.

A triphasic pulse can applied and the amplitude of the third phase selected so that the total electrical charge introduced equals zero. See Zimmerling M, *Messung des elektrisch evozierten Summenaktionspotentials des Hörnervs bei Patienten mit einem Cochlea-Implantat*, PhD thesis Universität Innsbruck, Institut für Angewandte Physik, 1999, and Schoesser H, Zierhofer C, Hochmair E S, *Measuring Electrically Evoked Compound Action Potentials Using Triphasic Pulses For The Reduction Of The Residual Stimulation Artefact*, In Conference On Implantable Auditory Prostheses, 2001; which are incorporated herein by reference. But the use of a triphasic pulse leads to an increased delay between the stimulus portion that triggers the NAPs and the beginning of the recording.

Another method records the response to a stimulus at sub-threshold level to measure a template for the stimulus artifact which is then scaled to supra-threshold levels and subtracted from the recorded signal mixture. See Miller C A, Abbas P J, Rubinstein J T, Robinson B, Matsuoka A, Woodworth G, *Electrically Evoked Compound Action Potentials Of Guinea Pig And Cat: Responses To Monopolar, Monophasic Stimulation*, Hearing Research 1998, 119(1-2):142-154; incorporated herein by reference. One disadvantage with that approach is that the artifact does not scale linearly with increasing amplitudes.

SUMMARY OF THE INVENTION

Embodiments of the present invention are directed to a method for processing an electrical stimulation response measurement waveform signal measured in response to delivery of a derived electrical stimulation signal to neural tissue. The electrical stimulation response measurement waveform signal contains a stimulus artifact and one or more neuronal action potentials. The electrical stimulation signal is derived based on satisfying a cost function comparison between at least one stimulus artifact component and a plurality of known neuronal action potential waveforms. The electrical stimulation response waveform signal is then processed using a source separation algorithm to remove the stimulus artifact component.

The neuronal action potentials may be an electrically evoked compound action potential, for example, as determined for a cochlear implant. The cost function may be based on a distance calculation between the stimulus artifact and the neuronal action potential waveforms, for example, based on maximizing the distance calculation. Satisfying the cost comparison may be based on a gradient descent procedure.

The method may further include applying the derived electrical stimulation signal to target neural tissue, measuring the waveform signal at the target tissue, and removing the stimulus artifact from the waveform signal using a source separation algorithm that leaves the neuronal action potential signal remaining.

DETAILED DESCRIPTION OF SPECIFIC EMBODIMENTS

Various embodiments of the present invention are directed to processing electrically evoked compound action potentials (ECAPs) signals in neuroprosthetic devices such as cochlear implants, which contain a stimulus artifact component and a neuronal action potentials (NAPs) component. An electrical stimulation signal is derived based on satisfying a cost function comparison with a plurality of known neuronal action potential waveforms. This allows improved removal of the stimulus artifact even in low signal-to-noise situations, for example, by using a matched filter that maximizes the output signal-to-noise ratio. There is no increase in measurement time compared to standard prior art waveform signal processing techniques. Automatic NAPs measurement is possible because the user does not need to set parameters manually, and, therefore, does not need any special technical knowledge.

In the context of signal processing, removing the stimulus artifact from an ECAP waveform signal mixture is known as a source separation problem. Robust separation of waveform components from some Source A (the stimulus artifact) from those due to another Source B (the NAP) is difficult because the two sources lack enough disjoint features. That is, they are too similar to achieve a good signal separation performance under the given signal-to-noise condition. To overcome this problem, embodiments of the present invention change the electrical stimulus waveform so that the resulting waveforms from the stimulus artifact and the triggered NAP are more diverse.

Figure 1:
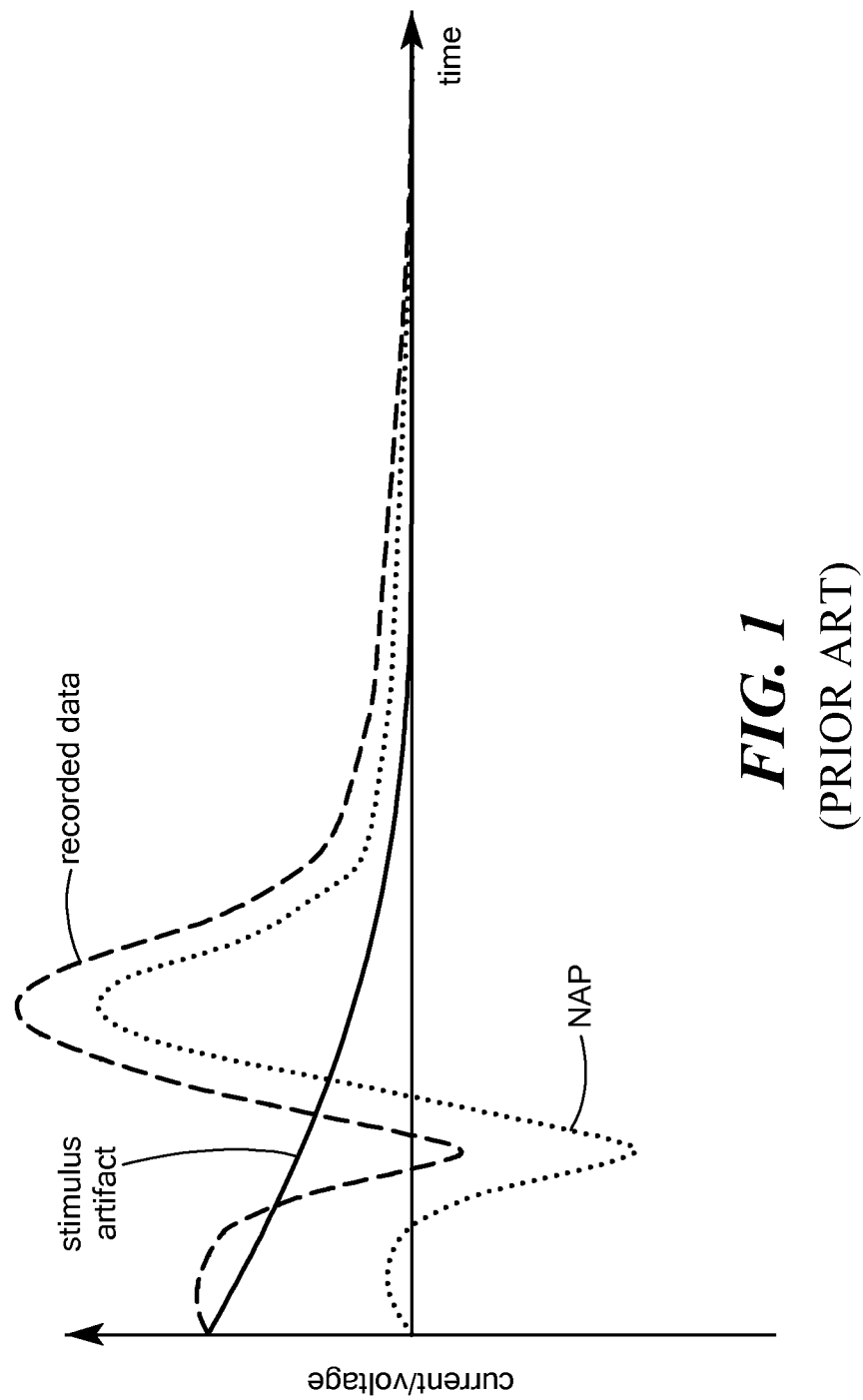
FIG. 1 shows ECAP related waveform signals as in a standard procedure according to the prior art.
Figure 2:
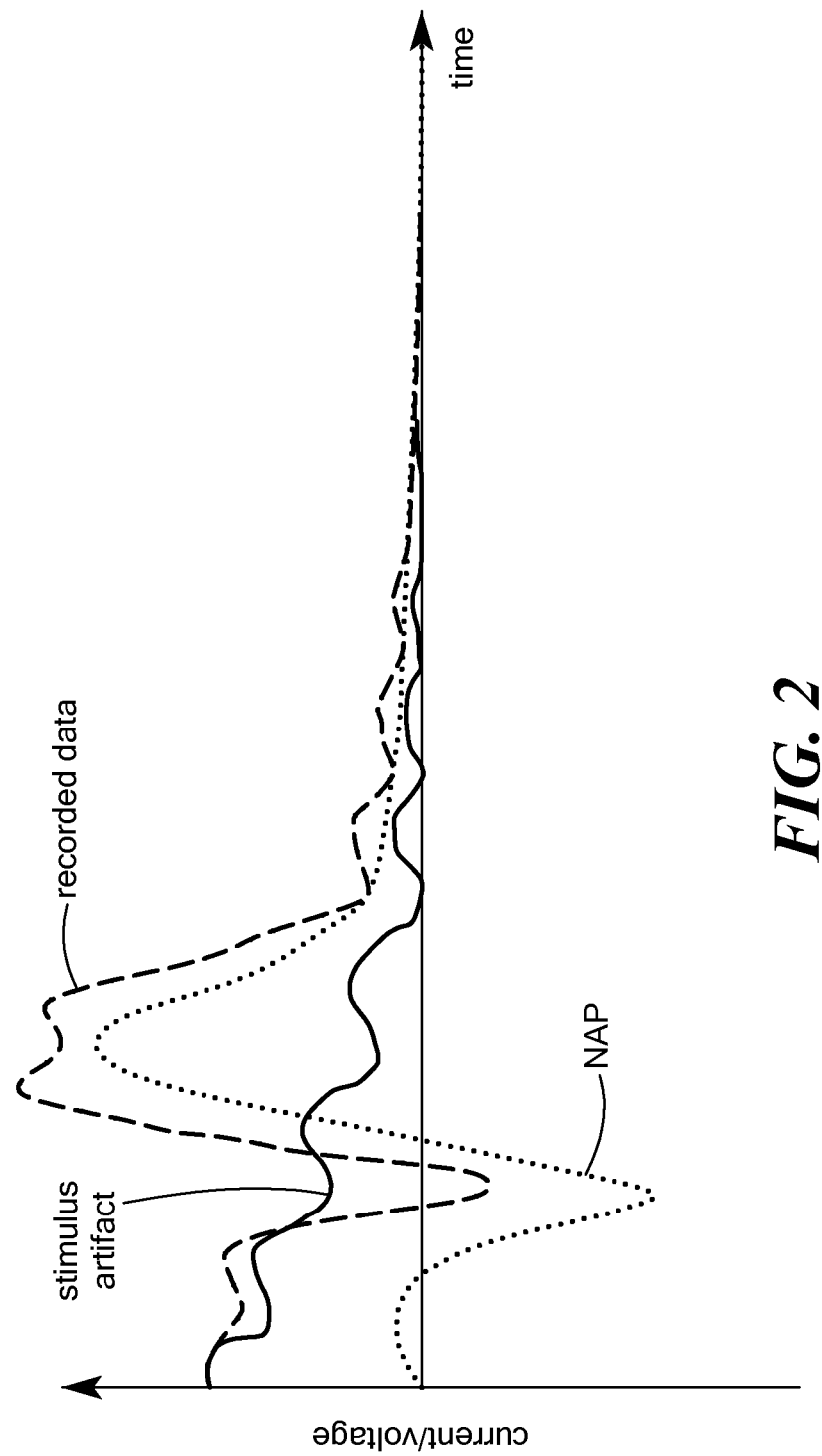
FIG. 2 shows ECAP related waveform signals according to an embodiment of the present invention.

FIG. 1 depicts ECAP related waveform signals as in a standard procedure according to the prior art. The stimulus artifact forms an exponentially decaying dc offset. By contrast, FIG. 2 shows how a stimulus artifact waveform differs from the NAP, in this case, by adding an oscillation with new features like minima and maxima (and therefore, a frequency component) which improves the source separation performance.

Initially, there are two situations where the derivation of a new stimulus artifact waveform can be performed. In a first embodiment, a general waveform is a priori derived using a database of existing NAP waveforms. For Source A (the stimulus artifact) a sampled waveform is defined as $x_A$ and for Source B (the NAP) another sampled waveform is defined as $x_B$, which are vectors of length N where N is the number of measured samples. As the performance of the source separation algorithm directly correlates with the distance of $x_A$ and $x_B$, an optimal new stimulus artifact waveform can be which maximizes this distance.

One simple way to measure such a distance would be a Euclidean metric, such that the new stimulus artifact waveform can be derived by maximizing a cost function:

$$C = sqrt((x_A(1) + x_{B1}(1))^2 + (x_A(2) + x_{B1}(2))^2 + \ldots + (x_A(N) + x_{B1}(N))^2) +$$
$$sqrt((x_A(1) + x_{B2}(1))^2 +$$
$$(x_A(2) + x_{B2}(2))^2 + \ldots + (x_A(N) + x_{B2}(N))^2) + \ldots +$$
$$sqrt((x_A(1) + x_{BM}(1))^2 + (x_A(2) + x_{BM}(2))^2 + \ldots + (x_A(N) + x_{BM}(N))^2)$$

with $x_m, \ldots, x_{BM}$ being the existing known NAP waveforms from a database and $x_A$ the vector of the possible stimulus artifact waveforms, which will be optimized. This is a standard optimization problem where algorithms such as a gradient descent search can be applied.

In a second embodiment, a patient dependent waveform is derived dynamically. The stimulus artifact waveform is known, so the achieved separation performance for the actual measurement can be derived. The measurement starts with the a priori derived waveform as described above. Using standard optimization algorithms such as a gradient descent search, the stimulus artifact waveform can be changed to be optimized for the actual measured waveform signal so as to achieve an improved separation performance.

Note that additional post-processing of $x_A$ and $x_B$ such as by a principle component analysis-based dimension reduction can further improve the performance of the waveform derivation. Also a more specialized metric such as a weighted metric may also show further improvements.

The fast identification of the Source A in the recorded waveform signal mixture can be performed using, for example, a matched filter approach which results in a source separation system that can operate in real-time. Besides using specific stimulus waveforms, which are kept constant during the optimization process, an alternative embodiment might use sub-optimal, but different stimuli.

Embodiments of the invention may be implemented in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A computer implemented method using at least one pre-programmed hardware element for processing an electrical stimulation response measurement waveform signal measured in response to delivery of a derived electrical stimulation signal to neural tissue, the electrical stimulation response measurement waveform signal containing a stimulus artifact component and a neuronal action potential component, the method comprising:

deriving the electrical stimulation signal based on satisfying an a priori cost function comparison between at least one defined possible stimulus artifact component and a plurality of known neuronal action potential waveforms;

applying the derived electrical stimulation signal to target neural tissue;

measuring the electrical stimulation response measurement waveform signal at the target tissue; and processing the measured electrical stimulation response measurement waveform signal using a source separation algorithm to remove the stimulus artifact component.

2. A method according to claim 1, wherein the neuronal action potential component is from an evoked compound action potential.

3. A method according to claim 2, wherein the evoked compound action potential is associated with a cochlear implant.

4. A method according to claim 1, wherein the cost function is based on a distance calculation between the stimulus artifact and the neuronal action potential waveforms.

5. A method according to claim 4, wherein the distance calculation uses a gradient descent procedure.

6. A method according to claim 4, wherein satisfying the cost comparison is based on maximizing the distance calculation.

7. A method according to claim 1, wherein the known neuronal action potential waveforms are a priori derived using a database of existing neuronal action potential waveforms.

8. A method according to claim 1, wherein the source separation algorithm uses a matched filter.

* * * * *